United States Patent [19]

Cetenko et al.

[11] 4,144,349

[45] Mar. 13, 1979

[54] N,N-DIMETHYL-1,2,4,5,6,7-HEXAHYDRO-THIOCINO[5,4-B]-INDOLE-7-PROPANA-MINE-3,3-DIOXIDES AND RELATED THIOCINES

[75] Inventors: Wiaczeslaw A. Cetenko; Glenn C. Morrison, both of Ann Arbor, Mich.

[73] Assignee: Warner-Lambert Company, Morris Plains, N.J.

[21] Appl. No.: 863,649

[22] Filed: Dec. 23, 1977

[51] Int. Cl.² .................... A61K 31/38; A61K 31/40; C07D 209/52

[52] U.S. Cl. ........................... 424/274; 260/326.5 SA; 260/326.9

[58] Field of Search .................. 260/326.5 SA, 326.9; 424/274

[56] References Cited

U.S. PATENT DOCUMENTS 3,776,922   12/1973   Epstein .................. 260/326.5 SA

*Primary Examiner*—Jose Tovar
*Attorney, Agent, or Firm*—Albert H. Graddis; Frank S. Chow; Anne M. Kelly

[57] ABSTRACT

This invention relates to novel compounds having the formula I:

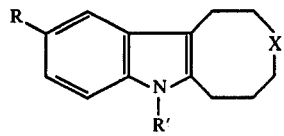

I wherein R is hydrogen, lower alkyl, lower alkoxy or halogen; R' is amino lower alkyl wherein the amino group is unsubstituted or substituted by mono- or di(-lower alkyl); and X is S or $SO_2$; and the non-toxic, pharmaceutically acceptable salts thereof, which are useful as antidepressants. Intermediates having the formula IV, which are used in the preparation of the compounds having the formula I are also disclosed:

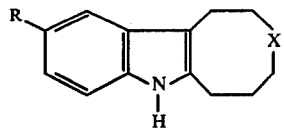

IV wherein R is hydrogen, lower alkyl, lower alkoxy or halogen; and X is S or $SO_2$.

22 Claims, No Drawings

N,N-DIMETHYL-1,2,4,5,6,7-HEXAHYDROTHIOCINO[5,4-B]-INDOLE-7-PROPANAMINE-3,3-DIOXIDES AND RELATED THIOCINES

BACKGROUND OF THE INVENTION

1. Field of the Invention

The present invention relates to substituted hexahydrothiocino[5,4-b]indole-7-alkylamines which are useful as antidepressants.

2. Description of the Prior Art 6,7,8,9,10,11-hexahydro-N,N-dimethyl-5H-cyclooct[b]indole-5-propanamine is an antidepressant known as Iprindole, prepared as described in U.S. Pat. No. 3,282,942. Iprindole is chemically distinct from the compounds claimed in the subject invention in a number of aspects, including the fact that no sulphur or sulphur dioxide moiety is present in the ring structure of Iprindole.

DESCRIPTION OF THE PARTICULAR EMBODIMENTS

This invention relates to novel hexahydrothiocino[5,4-b]indoles of the formula I:

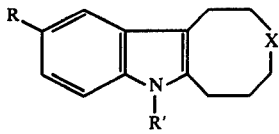

wherein R is hydrogen, lower alkyl, lower alkoxy, or halogen; R' is amino lower alkyl wherein the amino group is unsubstituted or substituted by a mono- or di(lower alkyl) group; and X is S or SO$_2$ and the non-toxic, pharmaceutically acceptable salts thereof. Compounds having the formula I have been found to have utility as antidepressants.

Preferred compounds of the invention are those having formula I wherein R is hydrogen, lower alkoxy or halogen; and R' is di(lower alkyl) amino lower alkyl, preferably wherein the lower alkyl group has from 1 to 3 carbon atoms. A particularly preferred embodiment of this invention includes compounds of the formula I wherein R is hydrogen, methoxy or bromo; and R' is dimethylaminopropyl, diethylaminopropyl, dimethylaminoethyl or diethylaminoethyl.

The compounds of the invention having the formula I are prepared by reacting a keto substituted thiocycloctane having the formula II:

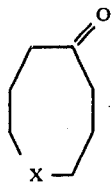

wherein X is S or SO$_2$ with a phenylhydrazine having the formula III:

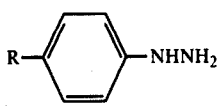

wherein R is hydrogen, lower alkyl, lower alkoxy or halogen to obtain the intermediate compound having the formula IV:

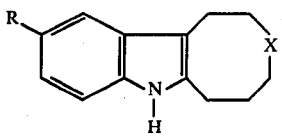

wherein R is hydrogen, lower alkyl, lower alkoxy or halogen; and X is S or SO$_2$.

The intermediate compound having the formula IV is then reacted with an amino alkyl chloride having the formula R'Cl (V) wherein R' is amino lower alkyl wherein the amino group is unsubstituted or substituted by a mono- or di(lower alkyl) group, to obtain the desired compound having the formula I.

Acid addition, non-toxic, pharmaceutically acceptable salts of the compounds having the formula I may be obtained by conventional methods, for example, by reaction of compound I with hydrogen chloride, hydrogen bromide and other suitable organic acids.

The starting material compound II, used in the above process is a known compound prepared as described in J. Am. Chem. Soc. 82: 4075–4085 (Aug. 5, 1960) by ring closure, hydrolysis and decarboxylation of diethyl γ,γ'-thia-bis-butyrate to obtain 1-thiacycloctane-5-one which is then oxidized with hydrogen peroxide to obtain the corresponding 1,1-dioxide; the aforementioned J. Am. Chem. Soc. 82: 4075–4084 (Aug. 5, 1960) is incorporated herein by reference.

Reagents III and V used in the above process are also known compounds, commercially available from Aldrich Chemical Co., Milwaukee, Wis.

In aforementioned formulas I–V, the following definitions apply: lower alkyl and the lower alkyl portion of lower alkoxy are meant to include straight or branched chain lower alkyl groups of 1 to 6 carbon atoms, preferably 1 to 3 carbon atoms; and halogen is meant to include chlorine, bromine and iodine.

The compounds of this invention having the formula I exhibit antidepressant activity in mammals as evidenced by positive results obtained in the Isolated Fighting Mouse Test (modification of the method of Yen, Stanger and Millman described in Arch. Intl. Pharmacodynamics, vol. 123, 1959) and in the Sidman Avoidance Test (method of M. Sidman, J. Comp. Physiol. Psychol. 46: 253–261, 1953 and Ann. N.Y. Acad. Sci. 65: 282–302, 1956; and P. Carlton, Pharmacologist 2:70, 1960 and 3:60, 1961).

In particular, N,N-dimethyl-1,2,4,5,6,7-hexahydrothiocino-[5,4-b]indole-7-propanamine 3,3-dioxide which is the compound of Example 6 has been shown to have Iprindole like activity in the Isolated Fighting Mouse Test and is active at a dose of 40 mg/kg when administered intraperitoneally. Additionally, N,N-dimethyl-1,2,4,5,6,7-hexahydrothiocino[5,4-b]indole-7-propanamine 3,3-dioxide can be considered superior to Iprindole in that it has an LD$_{50}$ in mice, when administered intraperitoneally, of 273 mg/kg while Iprindole has an LD$_{50}$ in mice, when administered intraperitoneally, of 81.6 mg/kg.

In the Sidman Avoidance Test (i.e., potentiation of d-amphetamine) N,N-dimethyl-1,2,4,5,6,7-hexahydrothiocino[5,4-b]indole-7-propanamine 3,3-dioxide is active at a dose of 5 mg/kg in rats when administered intraperitoneally.

Thus, the compounds of this invention having the formula I may be formulated with inert excipients into various dosage forms by methods well known to those skilled in the pharmacists art for oral or parenteral administration to mammals such as mice, rats, dogs and the like at dosage levels of from 5 to 50 mg/kg of body weight. Tablets, capsules, powders, solutions or suspensions are included among these dosage forms. Typically, for parenteral administration, the compounds having the formula I may be dissolved or suspended in 0.5% methylcellulose aqueous solution. For oral administration, the compounds of this invention having the formula I are formulated into dosage forms with inert diluents such as lactose. Dosage levels may be varied greatly, depending on the route of administration, species or condition being treated.

In order to further illustrate this invention, the following examples are provided:

EXAMPLE 1

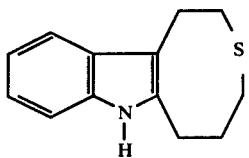

1,2,4,5,6,7-Hexahydrothiocino[5,4-b]indole

A mixture of 7.2g (0.05 mole) of 1-thiacyclooctane-5-one and 6.0g (0.056 mole) of phenylhydrazine in 40 ml of glacial acetic acid is refluxed for three hours under nitrogen. On standing there is deposited 5.2g of a solid, m.p. 106°–107° C. Recrystallization from cyclohexane affords 4.9g (45%) of an analytical sample m.p. 109°–110° C.

ANALYSIS: Calcd. for $C_{13}H_{15}N$ S:C, 71.84; H, 6.96; N, 6.44; S, 14.75. Found: C, 71.78; H, 7.09; N, 6.36; S, 14.67.

EXAMPLE 2

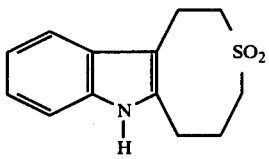

1,2,4,5,6,7-Hexahydrothiocino[5,4-b]indole 3,3-dioxide

A mixture of 35.34g (0.2 mole) of 1-thiacyclooctane-5-one 1,1-dioxide and 23.8g (0.22 mole) of phenylhydrazine in 250 ml of glacial acetic acid is refluxed for six hours under nitrogen. On standing there is deposited a crystalline solid which after recrystallization from methanol gives 40g (80%) of an analytical sample, m.p. 207°–208° C.

ANALYSIS: Calcd. for $C_{13}H_{15}NO_2S$: C, 62.62; H, 6.06; N, 5.62; S, 12.86. Found: C, 62.69; H, 6.18; N, 5.47; S, 12.70.

EXAMPLE 3

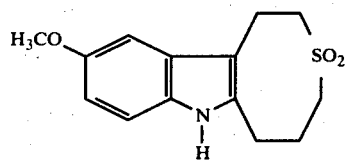

1,2,4,5,6,7-Hexahydro-10-methoxythiocino[5,4-b]indole 3,3-dioxide

A mixture of 26.54g (0.15 mole) of 1-thiacyclooctane-5-one 1,1-dioxide and 22.0g (0.16 mole) of p-methoxyphenylhydrazine in 150 ml of glacial acetic acid is treated according to the procedure in Example 2. There is obtained 36.7g (88%) of a crystalline solid, m.p. 231°–233° C. Recrystallization from acetone-ethyl acetate gives 30g (72%) of an analytical sample, m.p. 233°–235° C.

ANALYSIS: Calcd. for $C_{14}H_{17}NO_3S$: C, 60.19; H, 6.13; N, 5.01; S, 11.48. Found: C, 60.29; H, 6.26; N, 5.02; S., 11.53.

EXAMPLE 4

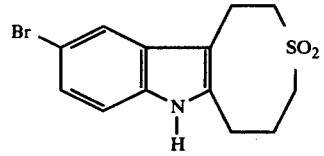

1,2,4,5,6,7-Hexahydro-10-bromothiocino[5,4-b]indole 3,3-dioxide

A mixture of 14.1g (0.08 mole) of 1-thiacyclooctane-5-one 1,1-dioxide and 16.1g (0.086 mole) of p-bromophenylhydrazine in 125 ml of glacial acetic acid is treated according to the procedure in Example 2. There is obtained 14.2g (54%) of a buff solid, m.p. 280° C., dec. Recrystallization from dimethylformamide-methanol gives 11.5g (44%) of an analytical sample, m.p. 283° C., dec.

ANALYSIS: Calcd. for $C_{13}H_{14}BrNO_2S$: C, 47.57; H, 4.30; N, 4.27; S, 9.77; Br, 24.35. Found: C, 47.74; H, 4.57; N, 4.36; S, 9.81; Br, 24.34.

EXAMPLE 5

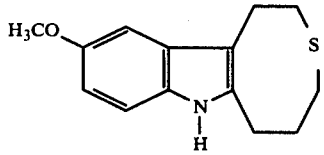

1,2,4,5,6,7-Hexahydro-10-methoxythiocino[5,4-b]indole

A mixture of 14.42g (0.1 mole) of 1-thiacyclooctane-5-one, 17.46g (0.1 mole) of p-methoxyphenylhydrazine hydrochloride and 8.21g (0.1 mole) of anhydrous sodium acetate in 170 ml of acetic acid is refluxed with stirring for five hours under nitrogen. The mixture is cooled and poured into 1 liter of water. On standing there is deposited a solid which after washing with water and recrystallization from methanol, gives 18.1g (74%) of an analytical sample, m.p. 122.5°–123.5° C.

ANALYSIS: Calcd. for $C_{14}H_{17}NOS$: C, 67.98; H, 6.93; N, 5.66; S, 12.96. Found: C, 68.07; H, 7.01; N, 5.74; S, 13.11.

EXAMPLE 6

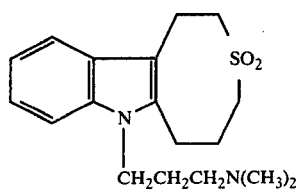

N,N-dimethyl-1,2,4,5,6,7-hexahydrothiocino[5,4-b]indole-7-propanamine 3,3-dioxide To a suspension of 2.1g (0.05 mole) of sodium hydride (57% dispersion in mineral oil) in 25 ml of dimethylformamide is added a solution of 12.47g (0.05 mole) of 1,2,4,5,6,7-hexahydrothiocino[5,4-b]indole 3,3-dioxide in 50 ml of dimethylformamide with stirring under nitrogen. The resulting mixture is stirred at 30°–35° C. for one hour. A solution of 6.03g (0.05 mole) of 3-dimethylaminopropyl chloride (freshly distilled) in 25 ml of dimethylformamide is added and the mixture is stirred at room temperature for one hour and then heated in a wax bath at 90° C. for five hours. The dimethylformamide is removed in vacuo. The residue is dissolved in 10% hydrochloric acid and extracted with ether. The aqueous layer is made basic with sodium hydroxide and extracted with ether. The ether layer is washed with water, dried over sodium sulfate and the solvent is removed. Recrystallization from isopropyl ether gives 10.7g (64%) of an analytical sample, m.p. 119°–120° C.

ANALYSIS: Calcd. for $C_{18}H_{26}N_2O_2S$: C, 64.64; H, 7.84; N, 8.37; S, 9.59. Found: C, 64.84; H, 7.84; N, 8.33; S, 9.42.

EXAMPLE 7

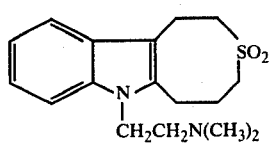

N,N-dimethyl-1,2,4,5,6,7-hexahydrothiocino[5,4-b]indole-7-ethanamine 3,3-dioxide A mixture of 12.47g (0.05 mole) of 1,2,4,5,6,7-hexahydrothiocino[5,4-b]indole 3,3-dioxide, 2.1g (0.05 mole) of 57% dispersion sodium hydride and 5.44g (0.05 mole) of 2-dimethylaminoethyl chloride is treated according to the procedure in Example 6. There is deposited 15.3g (96%) of a solid, m.p. 154°–155° C. Recrystallization from ethyl acetate gives 11.2g (70%) of an analytical sample, m.p. 155°–156° C.

ANALYSIS: Calcd. for $C_{17}H_{24}N_2O_2S$: C, 63.72; H, 7.55; N, 8.74. Found: C, 63.75; H, 7.70; N, 8.80.

EXAMPLE 8

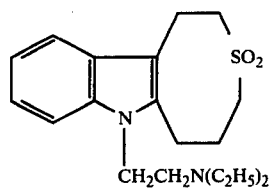

N,N-diethyl-1,2,4,5,6,7-hexahydrothiocino[5,4-b]indole-7-ethanamine 3,3-dioxide

A mixture of 14.9g (0.06 mole) of 1,2,4,5,6,7-hexahydrothiocino[5,4-b]indole 3,3-dioxide, 2.78g (0.066 mole) of 57% dispersion sodium hydride and 8.15g (0.06 mole) of 2-diethylaminoethyl chloride is treated according to the procedure in Example 6. There is obtained 20g (96%) of a solid, m.p. 118°–120° C. Recrystallization from isopropyl ether gives 17.1g (77%) of an analytical sample, m.p. 119°–120° C.

ANALYSIS: Calcd. for $C_{19}H_{28}N_2O_2S$: C, 65.48; H, 8.10; N, 8.04; S, 9.20. Found: C, 65.77; H, 8.25; N, 8.02; S, 9.45.

EXAMPLE 9

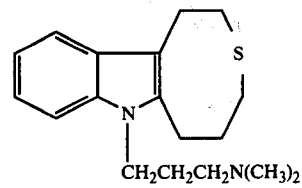

N,N-dimethyl-1,2,4,5,6,7-hexahydrothiocino[5,4-b]indole-7-propanamine

A mixture of 21.7g (0.1 mole) of 1,2,4,5,6,7-hexahydrothiocino-[5,4-b]indole, 4.29g (0.102 mole) of 57% dispersion sodium hydride and 12.16g (0.1 mole) of 3-dimethylaminopropyl chloride is treated according to the procedure in Example 6. Recrystallization from pentane affords 20.5g (69%) of an analytical sample, m.p. 70°–71° C.

ANALYSIS: Calcd. for $C_{18}H_{26}N_2S$: C, 71.47; H, 8.66; N, 9.26; S, 10.60. Found: C, 71.58; H, 8.63; N, 9.31; S, 10.76.

EXAMPLE 10

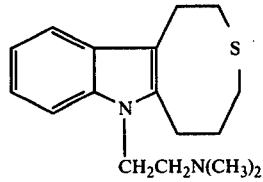

N,N-dimethyl-1,2,4,5,6,7-hexahydrothiocino[5,4-b]indole-7-ethanamine

A mixture of 10.9g (0.05 mole) of 1,2,4,5,6,7-hexahydrothiocino[5,4-b]indole, 2.1g (0.05 mole) of 57% dispersion sodium hydride and 5.44g (0.05 mole) of 2-dimethylaminoethyl chloride is treated according to the procedure in Example 6. There is obtained 11g (77%) of a solid, which after recrystallization from pentane, gives 7.1g (50%) of an analytical sample, m.p. 62°–64° C.

ANALYSIS: Calcd. for $C_{17}H_{24}N_2S$: C, 70.79; H, 8.39; N, 9.71; S, 11.12. Found: C, 70.90; H, 8.46; N, 9.56; S, 11.26.

EXAMPLE 11

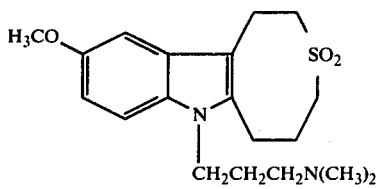

N,N-dimethyl-1,2,3,4,5,6,7-hexahydro-10-methoxythiocino[5,4-b]indole-7-propanamine 3,3-dioxide A mixture of 20.0g (0.072 mole) of 1,2,4,5,6,7-hexahydro-10-methoxythiocino[5,4-b]indole 3,3-dioxide, 3.07g (0.073 mole) of 57% dispersion sodium hydride and 8.75g (0.072 mole) of 3-dimethylaminopropyl chloride is treated according to the procedure in Example 6. Recrystallization from ether gives 14.9g (57%) of an analytical sample, m.p. 108°–110° C.

ANALYSIS: Calcd. for $C_{19}H_{28}N_2O_3S$: C, 62.61; H, 7.74; N, 7.69; S, 8.80. Found: C, 62.64; H, 7.68; N, 7.64; S, 8.99.

EXAMPLE 12

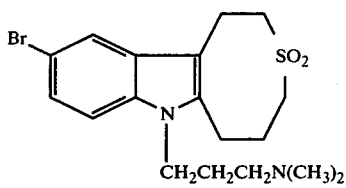

N,N-dimethyl-1,2,4,5,6,7-hexahydro-10-bromothiocino[5,4-b]indole-7-propanamine 3,3-dioxide A mixture of 9.0g (0.0276 mole) of 1,2,4,5,6,7-hexahydro-10-bromothiocino[5,4-b]indole 3,3-dioxide, 1.3g (0.03 mole) of 57% dispersion sodium hydride and 3.36g (0.0276 mole) of 3-dimethylaminopropyl chloride is treated according to the procedure in Example 6. After recrystallization from ethyl acetate, there is obtained 6.0g (52%) of an analytical sample, m.p. 135°–137° C.

ANALYSIS: Calcd. for $C_{18}H_{25}BrN_2SO_2$: C, 52.30; H, 6.10; N, 6.78; S, 7.76; Br, 19.33. Found: C, 52.32; H, 6.12; N, 6.73; S, 7.93; Br, 19.51.

EXAMPLE 13

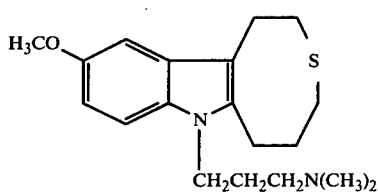

N,N-dimethyl-1,2,4,5,6,7-hexahydro-10-methoxythiocino[5,4-b]indole-7-propanamine.

A mixture of 11.2g (0.045 mole) of 1,2,4,5,6,7-hexahydro-10-methoxythiocino[5,4-b]indole, 2.12g (0.05 mole) of 57% dispersion sodium hydride and 5.5g (0.045 mole) of 3-dimethylaminopropyl chloride is treated according to the procedure in Example 6. Recrystallization from isopropyl ether affords an analytical sample, m.p. 79°–80° C.

ANALYSIS: Calcd. for $C_{19}H_{28}N_2OS$: C, 68.63; H, 8.49; N, 8.43; S, 9.64. Found: C, 68.71; H, 8.72; N, 8.21; S, 9.45.

We claim:

1. A compound of the formula I:

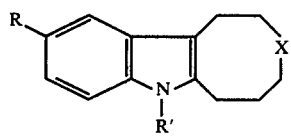

wherein R in hydrogen, lower alkyl, lower alkoxy or halogen; R' is amino lower alkyl wherein the amino group is unsubstituted or substituted by mono- or di(lower alkyl); and wherein, in R and R', the lower alkyl and lower alkoxy substituents contain 1 to 6 carbon atoms; and X is S or $SO_2$; and the non-toxic pharmaceutically acceptable acid-addition salts thereof.

2. A compound according to claim 1 wherein R' is di(lower alkyl) amino lower alkyl wherein the lower alkyl substituents contain 1 to 6 carbon atoms.

3. A compound according to claim 2 wherein R is hydrogen, lower alkoxy or halogen; R' is di(lower alkyl) amino lower alkyl; and wherein, in R and R', the lower alkyl and lower alkoxy substituents have 1 to 3 carbon atoms.

4. A compound according to claim 1 wherein R is hydrogen, methoxy or bromo; and R' is dimethylaminopropyl, diethylaminopropyl, dimethylaminoethyl or diethylaminoethyl.

5. The compound according to claim 1 which is N,N-dimethyl-1,2,4,5,6,7-hexahydrothiocino[5,4-b]indole-7-propanamine 3,3-dioxide.

6. The compound according to claim 1 which is N,N-dimethyl-1,2,4,5,6,7-hexahydrothiocino[5,4-b]indole-7-ethanamine 3,3-dioxide.

7. The compound according to claim 1 which is N,N-diethyl-1,2,4,5,6,7-hexahydrothiocino[5,4-b]indole-7-ethanamine 3,3-dioxide.

8. The compound according to claim 1 which is N,N-dimethyl-1,2,4,5,6,7-hexahydrothiocino[5,4-b]indole-7-propanamine.

9. The compound according to claim 1 which is N,N-dimethyl-1,2,4,5,6,7-hexahydrothiocino[5,4-b]indole-7-ethanamine.

10. The compound according to claim 1 which is N,N-dimethyl-1,2,3,4,5,7,-hexahydro-10-methoxythiocino[5,4-b]indole-7-propanamine 3,3-dioxide.

11. The compound according to claim 1 which is N,N-dimethyl-1,2,4,5,6,7-hexahydro-10-bromothiocino[5,4-b]indole-7-propanamine 3,3-dioxide.

12. The compound according to claim 1 which is N,N-dimethyl-1,2,4,5,6,7-hexahydro-10-methoxythiocino[5,4-b]indole-7-propanamine.

13. A compound of the formula IV:

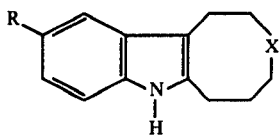

IV wherein R is hydrogen, 1 to 6 carbon lower alkyl, 1 to 6 carbon lower alkoxy or halogen; and X is S or $SO_2$.

14. A compound according to claim 13 wherein R is hydrogen, 1 to 6 carbon lower alkoxy or halogen.

15. A compound according to claim 13 wherein R is hydrogen, methoxy or bromo.

16. The compound according to claim 13 which is 1,2,4,5,6,7-hexahydrothiocino[5,4-b]indole.

17. The compound according to claim 13 which is 1,2,4,5,6,7-hexahydrothiocino[5,4-b]indole 3,3-dioxide.

18. The compound according to claim 13 which is 1,2,4,5,6,7-hexahydro-10-methoxythiocino[5,4-b]indole 3,3-dioxide.

19. The compound according to claim 13 which is 1,2,4,5,6,7-hexahydro-10-bromothiocino[5,4-b]indole 3,3-dioxide.

20. The compound according to claim 13 which is 1,2,4,5,6,7-hexahydro-10-methoxythiocino[5,4-b]indole.

21. A pharmaceutical composition for alleviating depression in mammals comprising an effective amount of a compound of the formula I:

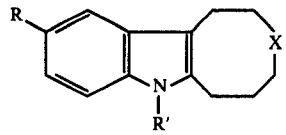

I wherein R is hydrogen, lower alkyl, lower alkoxy or halogen; R' is amino lower alkyl wherein the amino group is unsubstituted or substituted by mono- or di(-lower alkyl); and wherein, in R and R', the lower alkyl and lower alkoxy substituents contain 1 to 6 carbon atoms; and X is S or $SO_2$; and the non-toxic pharmaceutically acceptable acid-addition salts thereof, together with an inert pharmaceutical carrier.

22. A method for alleviating depression in mammals which comprises the administration of an effective amount of a compound of the formula I:

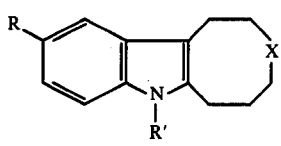

I wherein R is hydrogen, lower alkyl, lower alkoxy or halogen; R' is amino lower alkyl wherein the amino group is unsubstituted or substituted by mono- or di(-lower alkyl); and wherein, in R and R', the lower alkyl and lower alkoxy substituents contain 1 to 6 carbon atoms; and X is S or $SO_2$; and the non-toxic, pharmaceutically acceptable acid-addition salts thereof.

* * * * *